(12) United States Patent
Harrold

(10) Patent No.: US 6,964,336 B2
(45) Date of Patent: Nov. 15, 2005

(54) CHILD RESISTANT CONTAINER FOR APPLICATOR

(75) Inventor: John E. Harrold, Bloomsbury, NJ (US)

(73) Assignee: Valley Design Inc., Bloomsburg, NJ (US)

( * ) Notice: Subject to any disclaimer, the term of this patent is extended or adjusted under 35 U.S.C. 154(b) by 248 days.

(21) Appl. No.: 10/453,079

(22) Filed: Jun. 3, 2003

(65) Prior Publication Data
US 2005/0011790 A1 Jan. 20, 2005

(51) Int. Cl.$^7$ .............................................. B65D 83/00
(52) U.S. Cl. ...................... 206/361; 206/363; 206/807
(58) Field of Search ............................. 206/15.2, 209, 206/210, 361, 363, 438, 807; 604/1

(56) References Cited

U.S. PATENT DOCUMENTS

| | | | |
|---|---|---|---|
| 4,121,727 A | 10/1978 | Robbins | |
| 4,159,780 A | 7/1979 | Romaine | |
| 4,337,869 A | 7/1982 | Guinle | |
| 4,353,868 A * | 10/1982 | Joslin et al. | 422/101 |
| 4,960,339 A * | 10/1990 | Iizuka et al. | 401/129 |
| 4,979,648 A * | 12/1990 | Montgomery et al. | 222/153.14 |
| 5,000,193 A | 3/1991 | Heelis | |
| 5,074,693 A * | 12/1991 | Iizuka et al. | 401/4 |
| 5,163,441 A * | 11/1992 | Monthony et al. | 600/572 |
| D336,955 S | 6/1993 | Hadaway | |
| D338,956 S | 8/1993 | Hadaway | |
| 5,296,234 A | 3/1994 | Hadaway | |
| 5,388,588 A * | 2/1995 | Nabai et al. | 600/567 |
| 6,032,811 A | 3/2000 | Marconi | |
| 6,197,574 B1 * | 3/2001 | Miyamoto et al. | 435/287.6 |
| 6,248,294 B1 * | 6/2001 | Nason | 422/58 |

* cited by examiner

Primary Examiner—David T. Fidei
(74) Attorney, Agent, or Firm—Kenneth P. Glynn

(57) ABSTRACT

A child resistant container for stick applicators is described that is directed to keeping children out of the container prior to use, and to secure the container and its contents after use. In one embodiment, the container includes a combination cap and plug. The plug has a first and a second position relative to the cap, and the cap is not removable when the plug is in its first position and pulled, and is removable when the plug is in its second position and pulled. In another embodiment, a plug cap cannot be removed from the container unless a bottom cap is rotated to a go radial position and pushed in. When it is pushed into the tube container, the applicator functions as a push rod to open the top cap. The used applicator may be reinserted in an altered orientation, e.g., shortened or turned upside down and inserted, with the bottom cap pushed in, and the top cap reinserted into the top, access to the used applicator is inhibited.

13 Claims, 4 Drawing Sheets

CHILD RESISTANT CONTAINER FOR APPLICATOR

BACKGROUND OF THE INVENTION

1. Field of the Invention

The present invention is directed to a child resistant container for stick-type applicators. Such applicator could be for taking samples, e.g. environmental testing, throat cultures, or for providing medication, e.g. in-mouth or rectal application of cancer treatments. The present invention containers are especially useful for preventing access to an applicator in the container after it has been used.

2. Information Disclosure Statement

The following patents are representative of the state of the art of present invention-related technology:

U.S. Pat. No. 4,121,727 describes a vial construction including a vial body portion, an open end on said body portion, a tapered rim surrounding said open end, a plug having an entry portion for guidance by said tapered rim, a plug engaging portion on the body portion adjacent to the tapered rim, an interference fit between the entry portion and the plug engaging portion to render the connection there between fluid tight, a locking ring mounted on the outside of the rim and having a flange extending over the rim toward the open end of the container, cam locking members engageable with the flange to lock the plug to the flange, and a cutaway portion on the flange to permit disengagement between the flange and the cam locking members when the plug is rotated to a predetermined circumferential position on the locking ring.

U.S. Pat. No. 4,159,780 describes a child resistant container, e.g. a child resistant medicine bottle, which comprises in combination a container having a neck, a plug or other closure insertable in the neck with the plane of its upper surface extending not substantially beyond the plane of the upper surface of the neck, and rotary interengaging means interengaging the closure and the container neck. A key adapted to overlie the closure has gravity-actuated pin and socket means capable of releasably interchanging the closure and the key. Upon application, the key is operative to engage the closure with the neck and to disengage it therefrom.

U.S. Pat. No. 4,337,869 describes a closure assembly which comprises two separable closure members which are pre-assembled in coaxially stacked relationship, with their top panels aligned in the same direction. The lower closure member of the stack assembly comprises locking elements which are pre-assembled in coaxially stacked relationship, with their top panels aligned in the same direction. The lower closure member of the stack assembly comprises locking elements which are engageable with cooperating locking elements on a container, thereby providing a child-resistant closure. The upper closure is a simple snap cap, plug cap, or other closure which is not child resistant. The upper closure is removably attached to the lower child-resistant closure by an interference fit between resilient attachment members integrally formed as parts of the upper and lower closures. The assembly can be separated, for use of the upper closure only for sealing the container, thereby providing a choice between a child-resistant and non child-resistant closure.

U.S. Pat. No. 4,979,648 describes a push-pull dispensing closure for a container includes a child resistant sleeve which is slidably retained between the closure dispensing cap and the closure base member. In its NORMAL position, the sleeve obstructs member. When the sleeve is pushed toward the base member to the READY position, the cap can be gripped for opening movement. The sleeve is molded with a resiliently deformable plastic into which a return force is introduced as the sleeve is pushed toward its READY position.

U.S. Pat. No. 5,000,193 describes a device for expressing liquid absorbed by the tip of a medical swab. The device comprises a barrel and a plunger slidable within the barrel for squeezing the tip of the swab. Liquid is discharged through a flow channel in the container or in the swab shaft. The device is useful particularly to recover small volumes of swab-absorbed liquid where necessary e.g. to carry out clinical essays.

U.S. Pat. No. 5,296,234 describes a stick like holder and packaging, including an overcap and a sealed, light, moisture and tamper resistant foil pouch, for a hardened, medicated matrix affixed to one end of the holder including detent means for releaseably mounting the overcap on the matrix end of the holder and with the holder having flat, label receiving handle at its other end and a flange to prevent swallowing the holder when placed in a patient's mouth to medicate or pre-medicate the patient.

U.S. Pat. No. 6,032,811 describes a child resistant cap assembly includes an outer cap member having a top wall and a substantially cylindrical side wall depending therefrom. On the exterior surface of the top wall is a key slot and an alignment aperture. An inner cap member for threadedly engaging a container neck is concentrically received within said outer cap member has a mark and key slot on its top wall. The outer cap member normally rotates independently of the inner cap member. When the outer cap member's alignment aperture registers with the mark on the inner cap member, the key slots are aligned allowing a key member to be inserted therethrough. Accordingly, the inserted key member is then rotated to simultaneously rotate the inner and outer cap. The top wall of the outer cap member also includes means for removably retaining the key thereon.

Notwithstanding the prior art, the present invention is neither taught nor rendered obvious thereby.

SUMMARY OF THE INVENTION

The present invention is directed to containers for stick applicators, such as strong or hazardous medication applications (e.g. cancer treatments), and sample sticks. The containers of the present invention have been created to accomplish a number of objectives. These include child resistant, i.e., the characteristic of inhibiting entry unless compound movement is applied intelligently, resealability in terms of after-use storage, and entry inhibition or prevention after use, as well as an advantageous tight seal on the shelf before use and in storage after use. Thus, in one embodiment, the present invention is a child resistant container for an elongated stick applicator that includes an elongated hollow tube having a closed bottom and an open top; a cap adapted to fit and slideably move within the open top of the tube with a predetermined cap-to-tube frictional resistance, the cap having a top portion adapted to receive and removably hold a plug; and, a reversible plug: The reversible plug has a first end with at least one first elongated member adapted to removably fit into the cap, and has a second end with at least one second elongated member adapted to removably fit into the cap. The first elongated member has a first predetermined length and the second elongated member has a second predetermined length, and the second predetermined length is greater than the first predetermined length. Additionally, the first elongated member is adapted to fit into the cap with a frictional resistance less than the predetermined cap-to-tube frictional resistance, the second elongated member is adapted to fit into the cap with a frictional resistance greater than the predetermined cap-to-tube frictional resistance.

When the aforesaid cap is fitted into the open top of the elongated hollow tube with the first elongated member of the plug inserted into the cap, the second elongated member of the plug protrude outwardly and above the open top of the tube to permit gripping of the plug for removal of the plug from the cap without removing the cap. Further, when the cap is fitted into the open top of the elongated hollow tube with the second elongated member of the plug inserted into the cap, both the plug and the cap may be removed from the tube together. Further, when the second elongated member is fitted into the cap and is inserted into the tube and pushed into the tube, neither the plug nor the tube protrude outwardly and above the open top, to thereby prevent gripping and removal of the plug and the cap from the tube.

Hence, a user may utilize the present invention container devices to safely store an applicator with child resistant features, remove the applicator and use it as intended, return the applicator and then close up the applicator so as to inhibit subsequent unauthorized entry.

In some preferred present invention embodiments, the open top of the tube includes at least one stop to set a maximum depth of insertion of the cap. The cap itself may have any means of holding the plug, e.g. a rod, prongs, a catch or the like. In some preferred embodiments, the cap includes a recess with a sidewall adapted to receive and removably hold the plug. The present invention child resistant cap and the second elongated member of the plug may each have cooperating interlocking members that permit the plug to be inserted and held within the cap until taken apart. This could be in addition to or as an alternative to tight fitting sides. Further, in some embodiments, the plug includes at least one stop to control the depth of insertion of at least the first elongated member into the cap.

In alternative embodiments of the present invention containers, the tubes have an open top and an open bottom. The open bottom is not pass-through, as it contains a non-removable, slideable bottom cap that functions as a top cap push piston (using the applicator as a push rod), functions as a child resistant feature and also aids in post-use lock up.

Thus, in another present invention, child resistant container for an elongated stick applicator, there is included: an elongated hollow tube having an open bottom and an open top; an insertable cap adapted to fit into the open top of the tube, the cap being adapted to fit completely into said tube so as to prevent griping and inhibit removal thereof; a slideable bottom cap located in the open bottom of the elongated tube.

The slideable bottom cap has an outward position relative to the tube, being a first position, and an inwardly nested position relative to tube, being a second position.

The slideable bottom cap has a stop radial position, being a child resistant position, wherein the slideable bottom cap is not able to be nested inwardly to the second position, and has a go radial position, wherein the slideable bottom cap is able to be nested inwardly to the second position. Further, when an applicator stick is contained in the tube, the insertable cap may be closed and fitted completely in the tube when the slideable bottom cap is in its first position, and said insertable cap may not be closed and fitted completely in the tube when the slideable bottom cap is in its second position, until the applicator stick is altered relative to said tube, e.g. reversed. Further, the slideable bottom cap requires positioning in the go radial position to be moveable from its first position to its second position.

When the applicator stick is altered relative to the tube by being reversed in its insertion into the tube, the insertable cap may be closed and fitted completely in the tube when the slideable bottom cap is in its second position.

In some preferred embodiments, the slideable bottom cap is rendered inaccessible by being fully inserted into the tube when moved from its first position to its second position. This may be accomplished by a ratchet, lock or force fit configuration. In yet other preference embodiments, the slideable bottom cap includes an internal stick applicator receiving recess.

BRIEF DESCRIPTION OF THE DRAWINGS

The present invention should be more fully understood when the specification herein is taken in conjunction with the drawings appended hereto wherein:

FIG. 7 shows a view with the applicator not used and the device child resistant;

FIG. 8 shows it with the slideable bottom cap rotated and pushed in to push the applicator against the cap to open the cap;

FIG. 9 shows the device with the applicator already used, and returned to the tube in a reversed orientation; and, FIG. 10 shows the device with the top cap pushed in, the slideable, rotatable bottom cap pushed in and the used applicator sealed therein.

DETAILED DESCRIPTION OF THE PRESENT INVENTION

Figure 1:
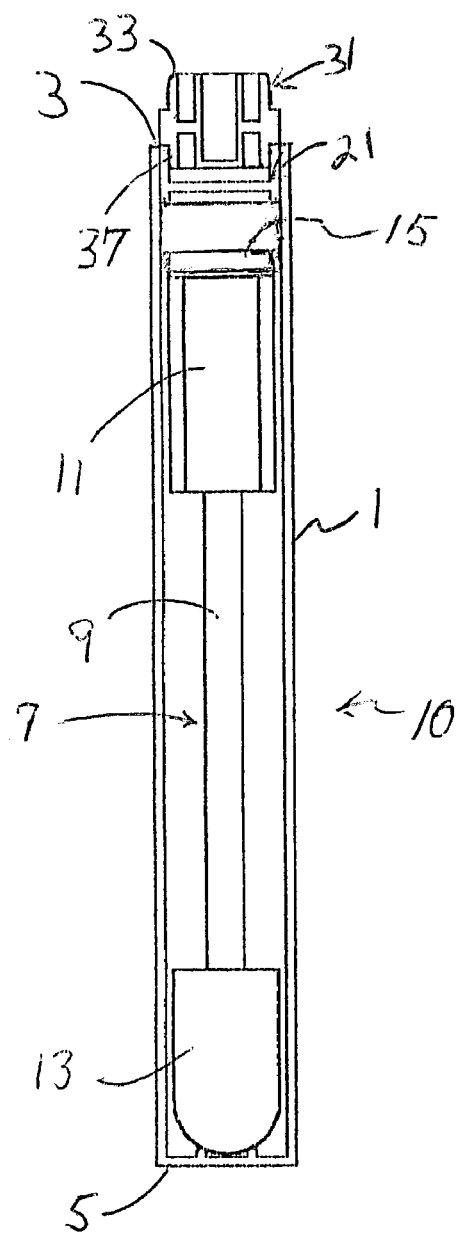
FIG. 1 shows a side cut view of one embodiment of a present invention child resistant container with an applicator.

FIG. 1 shows a side cut view of one embodiment of a present invention child resistant container 10 with an applicator 7. As can be seen in FIG. 1, the present invention. Child resistant container 10 includes an elongated hollow tube 1. Having an open top 3 and a close bottom 5. At a predetermined depth at open top and an annular stop 15. Inside container 10 is an elongated stick applicator 7. Applicator 7 includes a central stick or shaft 9, a handle 11 and a functional member 13. Functional member 13 could be a swab, a foam applicator tip, or a drug delivery element. Such as an oral medication matrix for treatment of cancer or other aliment. The widest cross section or diameter of applicator 7 is less than the diameter of stop 15 so that applicator 7 will pass by stop 15 for removal thereof from container 10.

Container 10 is fitted at top 3 with a two piece system made up of cap 21 and reversible plug 31, having an extended member 33. As shown in FIG. 1, the cap 21 is flush with top 3 and first elongated member 37 of plug 31, has a frictional resistance with cap 21 such that when plug 31 is pulled (as shown in FIG. 1), plug 31 pulls out of cap 21. This occurs because the cap-to-tube frictional resistance is greater than the frictional resistance between first elongated member 37 and cap 21. This renders child resistant container 10 unopenable. However for a smart user, i.e., a user who has the requisite knowledge to open container 10 may reverse plug 31 (turn upside down) and insert back in to cap 21 by then pulling the reverse plug 31, both the plug 31 and cap 21 will be removed.

Figure 2:
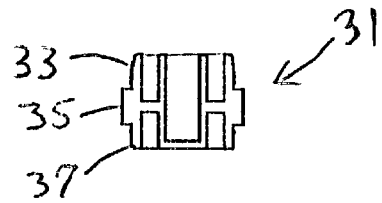
FIG. 2 shows details of the reversible plug of the FIG. 1 present invention device.
Figure 3:
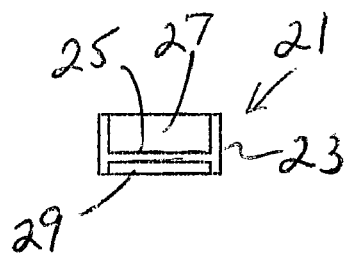
FIG. 3 shows a side cut view of the cap of the FIG. 1 present invention device.
Figure 4:
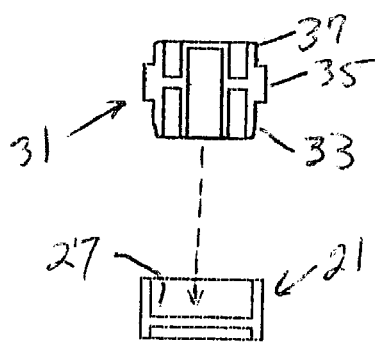
FIG. 4 illustrates the reversible plug of FIGS. 1 and 2 in its reversed position, being inserted into the removable cap.

Further details are illustrated in FIGS. 2, 3 and 4. In FIG. 2 a detail of plug 31 is illustrated with a first elongated member 37 extends below greater diameter mid section 35, and second elongated member 33 extending upwardly therefrom. As mentioned, when cap 21 is in container 10, member 37 of plug 31 does not have friction to remain engaged with cap 21 when pulled therefrom, but member 33 does have enough friction to hold cap 21 so that both are removed when plug 31 is inserted into cap 21 as shown in FIG. 5.

FIG. 3 shows a side cut view of the cap 21 of FIG. 1 above. Cap 21 has a cylindrical side wall 23, a central base 25 and recesses 29 and 27. As mentioned above, the plug 31 may be inserted into cap 21 and recessed 27 is adapted to receive either member 37, as shown in FIG. 1, or member 33 as shown in FIG. 4.

Figures 5, 6:
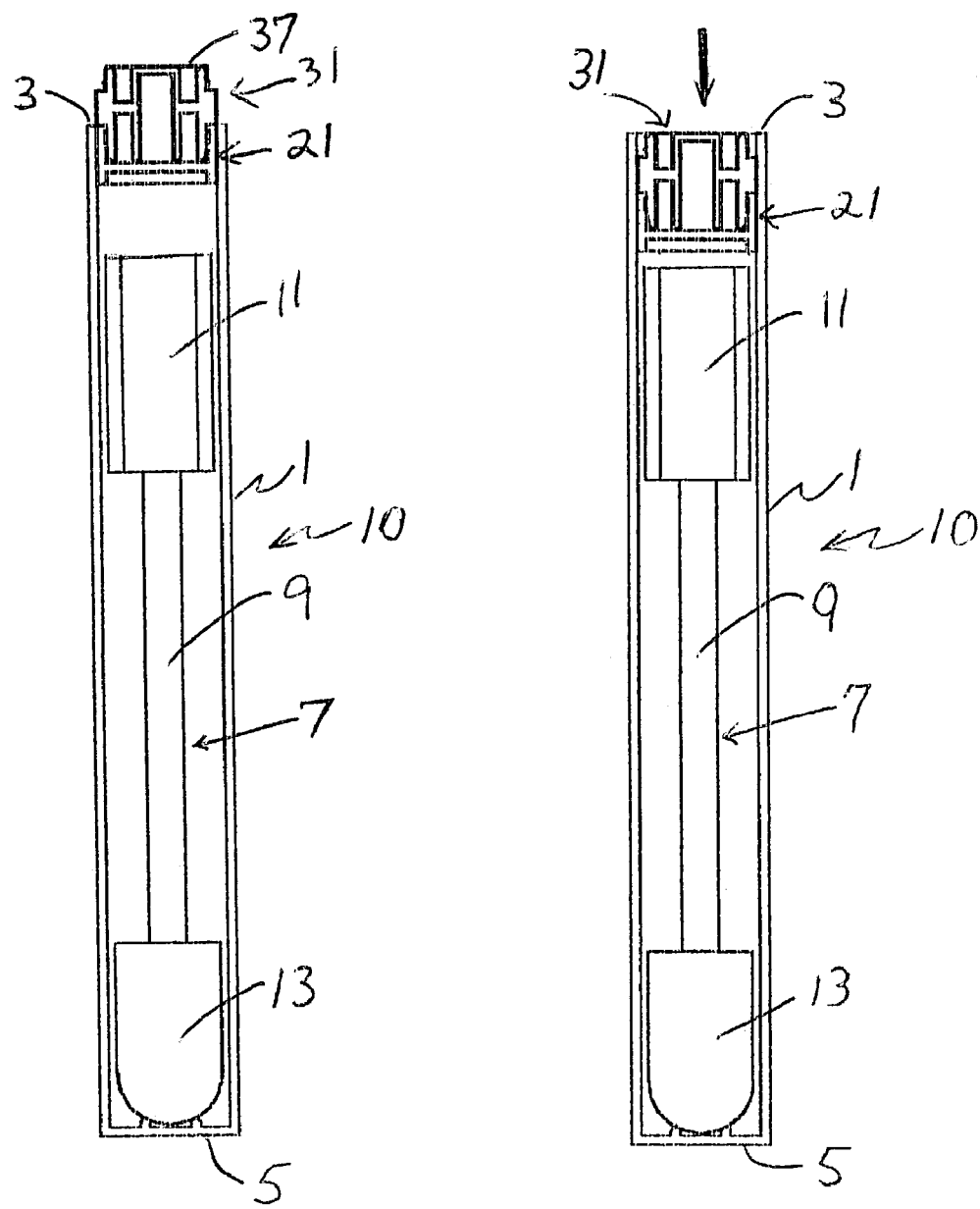
FIG. 5 shows the FIG. 1 present invention device, except that the plug is reversed and the cap is ready for removal to access the applicator for use.
FIG. 6 shows the FIGS. 1 and 5 present invention device after the applicator has been used and reinserted into the tube to render them non-removable and to the thus seal up the used applicator.

FIG. 5 shows the FIG. 1 present invention device, except that the plug 31 is reversed and the cap 21 is ready for removal to access the applicator for use. In FIG. 5, identical components are identically numbered, and need not be repeated. Likewise for FIG. 6, which shows the FIGS. 1 and 5 present invention device after the applicator 7 has been used and reinserted into the container 10 to render them non-removable and to thus seal up the used applicator 7 to prevent accidental exposure to children, and/or to prevent contamination.

FIGS. 7 through 10 show a side cut view of another embodiment of the present invention device 100 wherein a container tube 101 is open at both ends, i.e., top 103 and bottom 105. One end has a plug cap 131, and the other end, i.e. bottom 105 has a child resistant slideable bottom cap 111 that acts as a piston for access to and removal of applicator 115.

Figure 7:
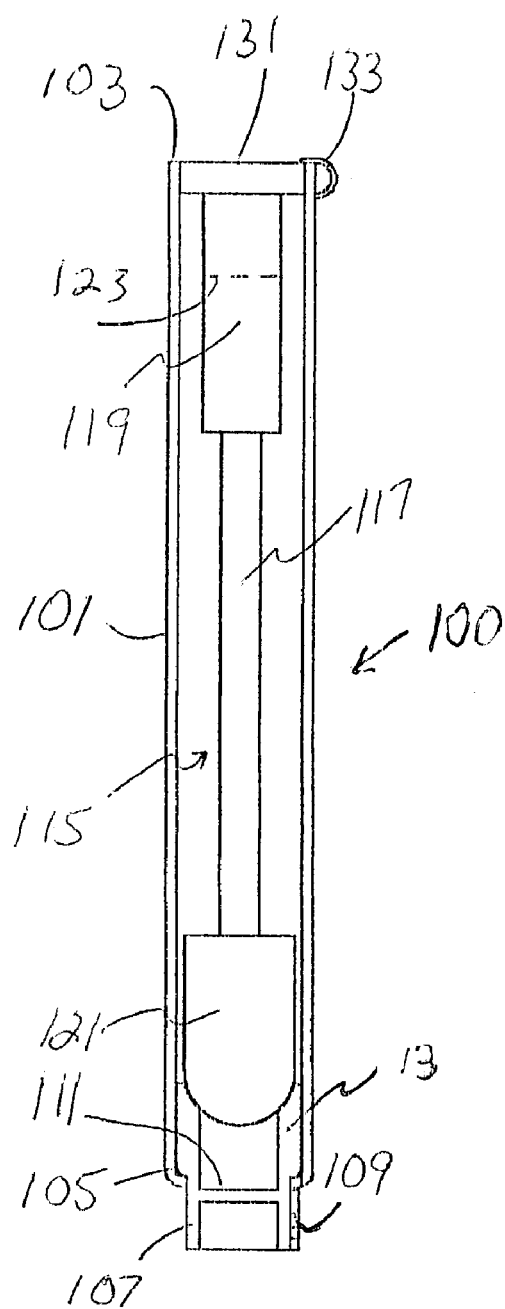
FIGS. 7 through 10 show side cut views of another embodiment of the present invention wherein a container tube is open at both ends, one end having a plug cap, and the other end having a child resistant slideable bottom cap that acts as a piston.

FIG. 7 shows a view with the applicator 115 not yet used and the device 100 child resistant. Here, container tube 101 has internally fitted plug cap 131 in a closed, non-removable position, in other words, because cap 31 is flat and is pushed into 101, cannot be removed from the top. Strap 133 keeps cap 131 connected to tube 101, but this is an optional convenience. In some preferred embodiments, cap 131 is unistructurally molded with tube 101 and a tether or strap to create a living hinge. Applicator 115 includes an elongated shaft 117, a handle 119 and an operative element 121. The operative element 121 has a greater maximum width then the maximum width of handle 119 such that handle 119 may fit into hollow cylinder portion 113 of slideable bottom cap 111 and such that the operative element 121 is too large to fit into hollow cylinder portion 113.

Figure 8:
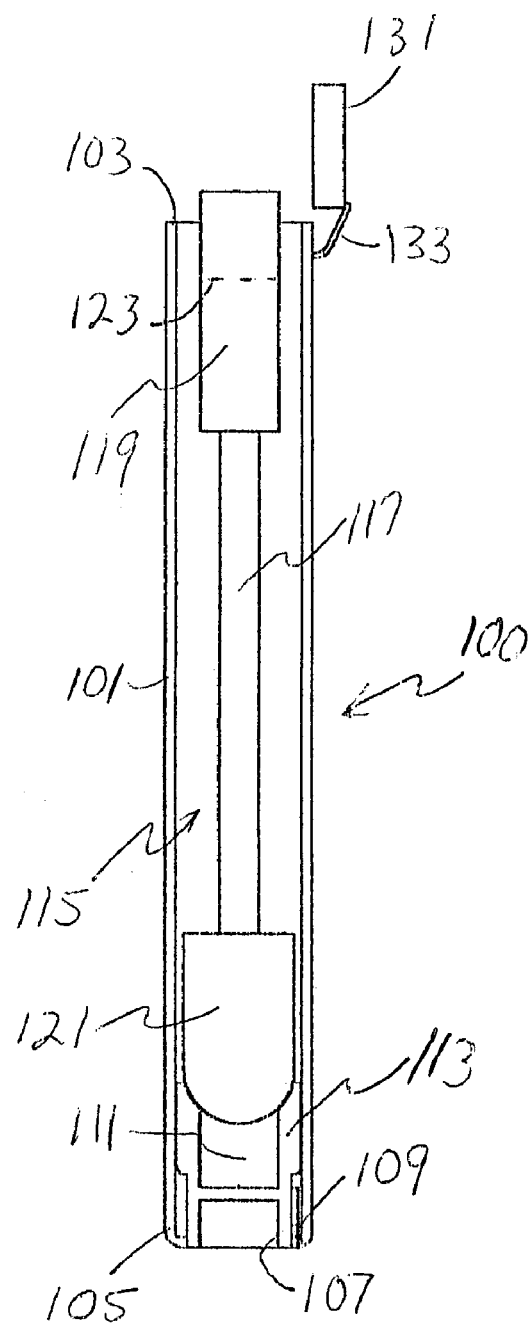

Referring specifically to FIGS. 7 and 8, with identical numbered components, bottom cap 111 has a protruding portion 107 that cannot be pushed into tube 101 unless it is positioned correctly. Thus, a user must rotate bottom cap 111 relative to tube 101 in order to move bottom cap 111 from a stop radial position to a go radial position. Wherein stop 109 or other stop element must fit an appropriate opening or key hole. As shown in FIG. 8, when bottom cap 111 is properly positioned and pushed inwardly into tube 101, bottom cap 111 acts as a piston and pushes applicator 115 upwardly to pop open top plug cap 131. The user may then remove applicator 115 for its intended use.

Figure 9:
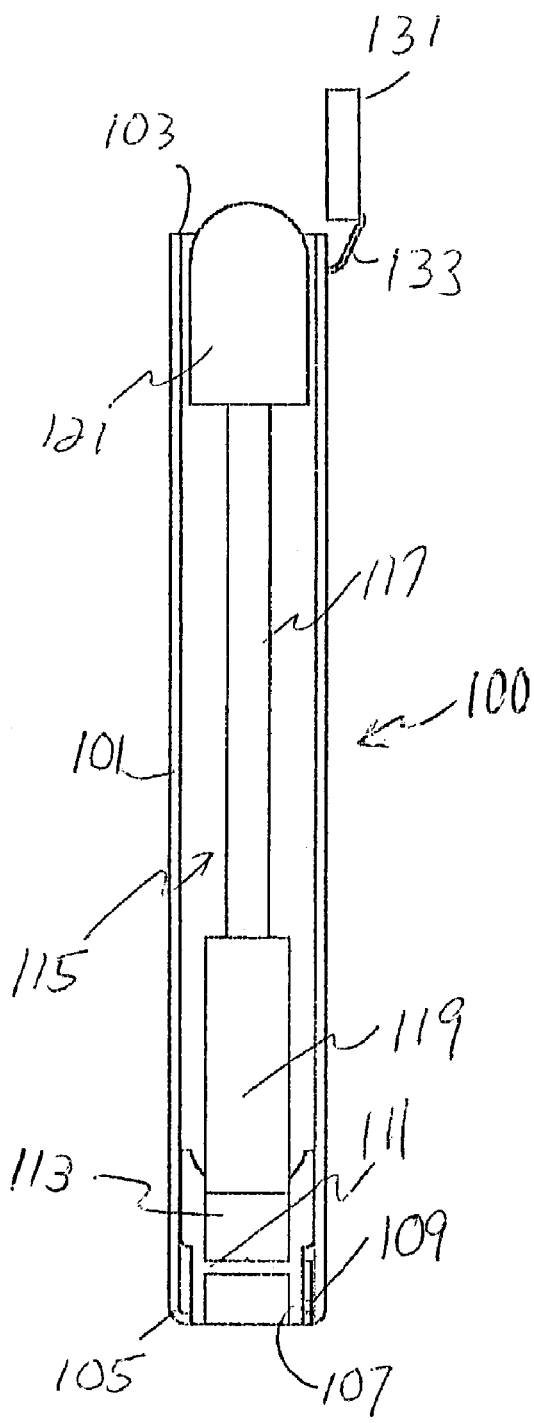
Figure 10:
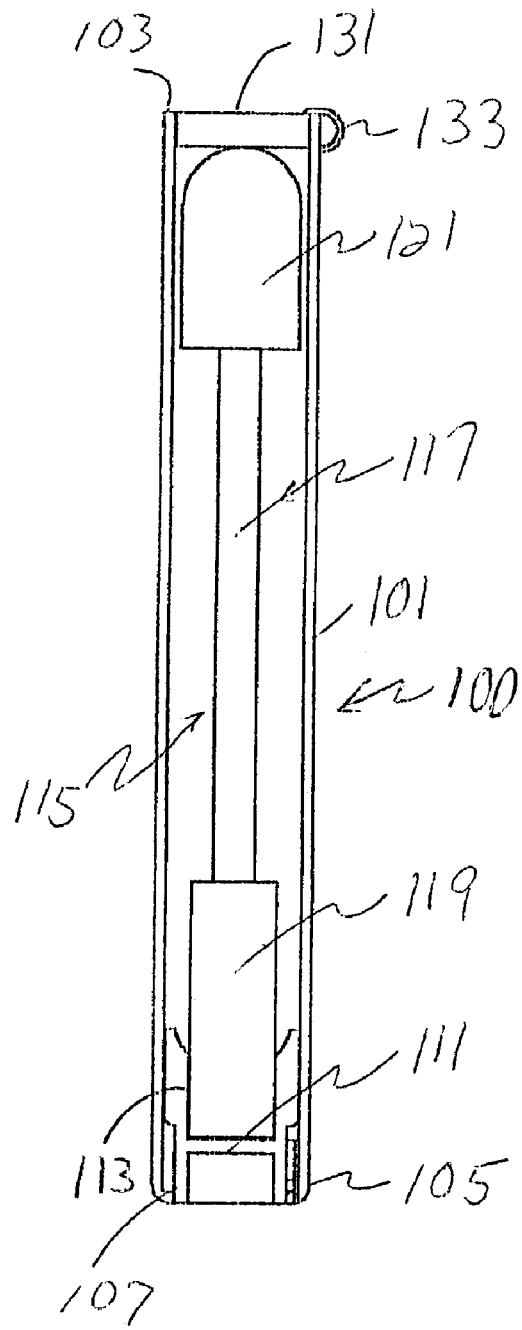

After use the applicator is returned to device 100 in the reverse position with handle 119 entering tube 101 first. Because handle 119 fits into hollow cylinder portion 113, as shown in FIG. 9. Next, cap 131 is reinserted into top 103 to seal up the used applicator 115 and render it again child resistant for proper disposal, e.g., medical waste or to a laboratory for testing or otherwise.

Obviously, numerous modifications and variations of the present invention are possible in light of the above teachings. It is therefore understood that within the scope of the appended claims, the invention may be practiced otherwise than as specifically described herein.

What is claimed is:

1. A child resistant container for an elongated stick applicator, which comprises:
    (a) an elongated hollow tube having an open bottom and an open top;
    (b) an insertable top cap adapted to fit into said open top of said tube, said cap being adapted to fit completely into said tube so as to prevent griping and inhibit removal thereof;
    (c) a slideable bottom cap located in said open bottom of said elongated tube, wherein said slideable bottom cap has an outward position relative to said tube, being a first position, and an inwardly nested position relative to said tube, being a second position;
    wherein said slideable bottom cap has a stop radial position, being a child resistant position, wherein said slideable bottom cap is not able to be nested inwardly to said second position, and has a go radial position, wherein said slideable bottom cap is able to be nested inwardly to said second position; and,
    such that, when an applicator stick is contained in said tube, said insertable cap may be closed and fitted completely in said tube when said slideable bottom cap is in its first position, and said insertable cap may not be closed and fitted completely in said tube when said slideable bottom cap is in its second position, until said applicator stick is altered relative to said tube, and such that said slideable bottom cap requires positioning in said go radial position to be moveable from its first position to its second position.

2. The child resistant container of claim 1 wherein, when said applicator stick is altered relative to said tube by being reversed in its insertion into said tube, said insertable top cap may be closed and fitted completely in said tube when said slideable bottom cap in its second position.

3. The child resistant container of claim 1 wherein, when said applicator stick is altered relative to said tube, said insertable top cap may be closed and fitted completely in said tube when said slideable bottom cap is altered relative to said tube by being shortened.

4. The child resistant container of claim 1 wherein said insertable cap includes a flexible connector connecting said cap to said tube.

5. The child resistant container of claim 1 wherein said tube is a cylindrical tube.

6. The child resistant container of claim 1 wherein said slideable bottom cap is rendered inaccessible by being fully inserted into said tube when moved from its first position to its second position.

7. The child resistant container of claim 1 wherein said slideable bottom cap includes an internal stick applicator receiving recess.

8. A child resistant container and an elongated stick applicator, which comprises:
   (a) an elongated hollow tube having an open bottom and an open top:
   (b) an insertable cap adapted to fit into said open top of said tube, said cap being adapted to fit completely into said tube so as to prevent griping and inhibit removal thereof;
   (c) an elongated stick applicator having a first end and a second end, said first end having an application element;
   (d) a slideable bottom cap located in said open bottom of said elongated tube, wherein said slideable bottom cap has an outward position, being a first position, and an inwardly nested position relative to said tube, being a second position;
   wherein said slideable bottom cap has a stop radial position, being a child resistant position, wherein said slideable bottom cap is not able to be nested inwardly to said second position, and has a go radial position, wherein said slideable bottom cap is able to be nested inwardly to said second position; and,
   such that, when an applicator stick is contained in said tube, said insertable cap may be closed and fitted completely in said tube when said slideable bottom cap is in its first position, and said insertable cap may not be closed and fitted completely in said tube when said slideable bottom cap is in its second position, until said applicator stick is altered relative to said tube, and such that said slideable bottom cap requires positioning in said go radial position to be moveable from its first position to its second position.

9. The child resistant container and elongated stick applicator of claim 8 wherein said elongated stick applicator first end has a first maximum width, said second end has a second maximum width, and said first maximum width is greater than said second maximum width.

10. The child resistant container and elongated stick applicator of claim 8 wherein when said applicator stick is altered relative to said tube by being reversed in its insertion into said tube, said insertable cap may be closed and fitted completely in said tube when said slideable bottom cap is in its second position.

11. The child resistant container and elongated stick applicator of claim 8 wherein, when said applicator stick is altered relative to said tube, said insertable cap may be closed and fitted completely in said tube when said slideable bottom cap is altered relative to said tube by being shortened.

12. The child resistant container and elongated stick applicator of claim 8 wherein said slideable bottom cap is rendered inaccessible by being fully inserted into said tube when moved from its first position to its second position.

13. The child resistant container and elongated stick applicator of claim 8 wherein said slideable bottom cap includes an internal stick applicator receiving recess.

* * * * *